United States Patent
Zimmermann et al.

(10) Patent No.: US 12,215,892 B2
(45) Date of Patent: Feb. 4, 2025

(54) METHOD FOR TESTING AN ELECTRODE ARRANGEMENT FOR GENERATING A NON-THERMAL PLASMA, AND PLASMA SOURCE HAVING AN ELECTRODE ARRANGEMENT OF THIS KIND AND CONFIGURED FOR PERFORMING A METHOD OF THIS KIND

(71) Applicants: terraplasma GmbH, Garching (DE); terraplasma medical GmbH, Garching (DE)

(72) Inventors: Julia Zimmermann, Munich (DE); Michael Linner, Garching (DE); Sylvia Cantzler, Ebersberg (DE); Gregor Morfill, Munich (DE); Hannes Weilemann, Munich (DE); Maximilian Cantzler, Ebersberg (DE)

(73) Assignees: terraplasma GmbH, Garching (DE); terraplasma medical GmbH, Garching (DE)

( * ) Notice: Subject to any disclaimer, the term of this patent is extended or adjusted under 35 U.S.C. 154(b) by 934 days.

(21) Appl. No.: 17/252,116

(22) PCT Filed: Jun. 13, 2019

(86) PCT No.: PCT/EP2019/065574
§ 371 (c)(1),
(2) Date: Dec. 14, 2020

(87) PCT Pub. No.: WO2019/238866
PCT Pub. Date: Dec. 19, 2019

(65) Prior Publication Data
US 2021/0259089 A1    Aug. 19, 2021

(30) Foreign Application Priority Data
Jun. 15, 2018 (DE) .......................... 102018209730.5

(51) Int. Cl.
*F24F 8/20* (2021.01)
*H05H 1/24* (2006.01)

(52) U.S. Cl.
CPC ............. *F24F 8/20* (2021.01); *H05H 1/2439* (2021.05); *B01D 2257/91* (2013.01); *H05H 2240/20* (2013.01); *H05H 2242/22* (2021.05)

(58) Field of Classification Search
CPC ........... H05H 2240/20; H05H 2242/22; H05H 1/2425; H05H 1/2439; H05H 1/0037; F24F 8/20; B01D 2257/91
See application file for complete search history.

(56) References Cited

U.S. PATENT DOCUMENTS

| 5,830,310 A | 11/1998 | Doi |
| 6,350,960 B1 | 2/2002 | Norris |

(Continued)

FOREIGN PATENT DOCUMENTS

| CN | 104756334 B | * 5/2017 | ............... A61L 2/14 |
| CN | 107787108 A | 3/2018 | |

(Continued)

OTHER PUBLICATIONS

English translation of International Search Report and Written Opinion for PCT/EP2019/065574 dated Oct. 15, 2019, 16 pages.

(Continued)

*Primary Examiner* — Octavia Hollington
(74) *Attorney, Agent, or Firm* — Sheppard Mullin Richter & Hampton LLP

(57) ABSTRACT

The invention relates to a method for testing an electrode arrangement (1) for generating a non-thermal plasma, having the following steps: determining at least one power parameter which characterizes a plasma power of the electrode arrangement (1); comparing the at least one power parameter with at least one predetermined target parameter (Continued)

value, and obtaining a comparison result; assessing the functionality of the electrode arrangement (1) on the basis of the comparison result, and preferably selecting at least one action according to the comparison result.

17 Claims, 3 Drawing Sheets

(56) References Cited

U.S. PATENT DOCUMENTS

| | | | | |
|---|---|---|---|---|
| 8,864,932 | B2 * | 10/2014 | Furuya | G05D 23/19 |
| | | | | 118/724 |
| 2014/0207053 | A1 | 7/2014 | Morfill et al. | |

FOREIGN PATENT DOCUMENTS

| | | | | |
|---|---|---|---|---|
| EP | 1243277 | B1 | | 9/2002 |
| EP | 1693014 | A1 * | 8/2006 | A61B 18/042 |
| EP | 2051741 | B1 | | 4/2009 |
| JP | 2001259409 | A | | 9/2001 |
| WO | 2015049780 | A1 | | 4/2015 |
| WO | 2017013211 | A1 | | 1/2017 |
| WO | 2017147625 | A2 | | 8/2017 |

OTHER PUBLICATIONS

Author Unknown, Dielectric barrier discharge, Apr. 16, 2018, Wikipedia [online], https://en.wikipedia.org/w/index.php?title=Dielectric_barrier_discharge&oldid=836695053.

English translation of the International Preliminary Report on Patentability for PCT/EP2019/065574 dated Dec. 15, 2020, 10 pages.

* cited by examiner

METHOD FOR TESTING AN ELECTRODE ARRANGEMENT FOR GENERATING A NON-THERMAL PLASMA, AND PLASMA SOURCE HAVING AN ELECTRODE ARRANGEMENT OF THIS KIND AND CONFIGURED FOR PERFORMING A METHOD OF THIS KIND

CROSS REFERENCE TO RELATED APPLICATIONS

This application is a U.S. National Stage Application under 35 U.S.C. 371 of International Application No. PCT/EP2019/065574, filed Jun. 13, 2019, which claims priority to German Patent Application No. 10 2018 209 730.5, filed Jun. 15, 2018. The contents of each of the aforementioned are hereby incorporated by reference in their entirety into the present disclosure.

The invention relates to a method for testing an electrode arrangement for generating a non-thermal plasma, as well as to a plasma source having such an electrode arrangement, the plasma source being configured to carry out such a method.

Non-thermal plasmas are used in a variety of applications to reduce a number of pathogenic germs or to eliminate such germs, for example in the treatments of wounds, the treatment of skin diseases, food hygiene, the production of water for intravenous injection, drinking water treatment, decontamination, disinfection or sterilization of objects, in particular medical devices and/or in the military sector, in the civil sector, in the aerospace sector, in particular for surface treatments, and more particularly surface sterilization or disinfection, the inactivation of allergens, seed treatment, crop protection, odor reduction, for example for freshening up textiles or textile products, especially clothing or mattresses, air purification and monitoring, and many more similar applications. Non-thermal plasmas are used for the treatment of wounds and for the treatment of skin diseases because, in addition to their germ load reducing effect, they also have healing effects. Many of these applications are critical in the sense that for the user or for the person on whom or for whom the application is carried out, for example a patient or a consumer of drinking water treated in this way, a user of seeds, or the like, significant dangers may be present if the non-thermal plasma is not generated and applied in the application, or is not generated to a sufficient extent. For safety reasons, it may also be necessary to comply with a limit for a maximum dose of certain species. In the case of a planar or geometrically linear plasma generation, it is also important to obtain information about whether the plasma is generated evenly along a surface or line on which it is to be generated; otherwise, there is a risk that certain areas or linear regions will be treated to a lesser extent or not at all, while other areas may be exposed to the plasma to an excessive extent.

There is therefore a need for a method with which it can be reliably determined whether an electrode arrangement for generating a non-thermal plasma is functioning according to requirements.

The invention is based on the object of creating a method for testing an electrode arrangement for generating a non-thermal plasma, which helps to avoid the disadvantages mentioned, in particular making it possible to check the electrode arrangement for proper functionality. The invention is also based on the object of creating a plasma source which has an electrode arrangement for generating a non-thermal plasma, the plasma source being configured to carry out the aforementioned method.

The object is achieved by creating the subject matter of the independent claims. Advantageous configurations are found in the dependent claims.

The object is achieved in particular by creating a method for testing an electrode arrangement for generating a non-thermal plasma, which has the following steps: At least one power parameter is determined which is characteristic of a plasma power of the electrode arrangement. The power parameter is determined in particular during operation, but before the electrode arrangement is used; it is particularly characteristic of a momentary plasma power of the electrode arrangement during its operation, but before use. The at least one determined power parameter is compared with at least one predetermined target parameter value, and a comparison result is obtained from this comparison. The functionality of the electrode arrangement is assessed on the basis of the comparison result. By means of the method proposed here, it is possible, particularly initially when the electrode arrangement is turned on, to reliably and precisely determine its functionality and thus to prevent dangers for a user of the electrode arrangement or for third parties which are associated with poor, reduced or non-existent functionality of the electrode arrangement. At least one action is preferably selected according to the comparison result. In this way it is possible to react to the comparison result and thus also to the assessed functionality of the electrode arrangement, and to select an action adapted to this.

A non-thermal plasma is understood in particular to be a plasma in which a temperature describing the distribution of the kinetic energy of electrons in the plasma, which is also referred to as the electron temperature, is not identical and in particular is very much higher than a temperature describing the distribution of the kinetic energy of the ions comprised by the plasma, in particular atomic ions and/or molecular ions, which is also referred to as the ion temperature. The electron temperature is very much higher than the ion temperature, wherein the ion temperature can be selected in the range from 25° C. to a maximum of 100° C. Such a plasma is also referred to as a cold plasma due to the comparatively low ion temperature.

A state of matter in which charged particles with positive and negative charges are present together in the gas phase, wherein there is a neutral electrical charge averaged over a certain volume for the volume under consideration, is referred to here as plasma. The plasma also preferably comprises uncharged atoms and/or molecules which are in electronically, vibratory and/or rotationally excited states, and which are also referred to as excited particles, and/or free radicals—and therefore overall, in particular uncharged reactive atoms and/or molecules, also known as reactive particles or reactive species.

An electrode arrangement is understood in this case, in particular, to mean an arrangement of electrically conductive electrodes relative to each other which is configured to generate a non-thermal plasma when a voltage, in particular an alternating voltage, is applied to the electrode arrangement. A plasma source is understood to mean a device which, in addition to the electrode arrangement in the narrower sense—that is, the arrangement of electrically conductive electrodes relative to each other—also comprises means for applying electrical power to the electrodes, in particular a voltage source, and preferably a control device for influencing, specifying, measuring, evaluating, controlling and/or regulating the current values applied to the electrodes, in particular a voltage and/or a current intensity.

The electrode arrangement preferably has a first electrode and a second electrode, which are spaced apart by a dielectric, such that plasma discharges, in particular surface microdischarges, can be generated on one of the two electrodes when a voltage, in particular an alternating voltage, is applied to the electrodes. The electrode arrangement is thus configured to generate a non-thermal plasma independently of a surface external to the electrode arrangement. In particular, the electrode arrangement is designed as an SMD (surface micro discharge) electrode arrangement. In particular, there is no need for a treatment surface to be included in the circuit as a counter electrode. The two electrodes of the electrode arrangement are preferably in physical contact with the dielectric; they can be embedded in the dielectric or arranged on the dielectric, for example by vapor deposition, screen printing, physical or chemical vapor deposition, by application or pressing, gluing, or in another suitable manner, wherein they are arranged tightly against the dielectric, and in particular without an air gap. Thus, in particular, both electrodes of the electrode arrangement are arranged on the same side of a treatment surface. In particular, the treatment surface is not arranged between the two electrodes of the electrode arrangement.

The electrode arrangement is configured in particular to generate a non-thermal plasma in air, in particular in ambient air. Accordingly, preferably no special gas is used to generate the non-thermal plasma, in particular no such special gas, in particular no carrier gas, is fed to the electrode arrangement.

The method proposed here is particularly suitable for testing such an electrode arrangement. In particular for such an electrode arrangement, the plasma power is also directly dependent on a surface or line along which or on which the plasma is generated, wherein any irregularities in the plasma generation and/or surface parts and/or linear regions on or in which no plasma is generated, for example due to contamination, directly reduce the plasma power. Thus, the comparison of the power parameter with the at least one predetermined target parameter value can be utilized to also determine whether the plasma is generated uniformly.

A plasma power of the electrode arrangement is understood to mean the portion of the electrical power consumed by the electrode arrangement which is used directly to generate the non-thermal plasma, and which is in particular directly related to a generation rate for reactive particles comprised by the plasma. If a parameter is captured as the power parameter that is characteristic of this plasma power, conclusions can be drawn in a particularly safe and reliable way about the functionality of the electrode arrangement, because the power parameter in this case provides direct information about the plasma generation by the electrode arrangement.

An assessment of the functionality of the electrode arrangement is understood to mean, in particular, that a statement about the functionality of the electrode arrangement is derived, either indirectly by selecting a certain action and/or directly by outing a message describing or identifying the functionality of the electrode arrangement. The functionality can be assessed in this case as a simple, binary determination, namely whether the electrode arrangement is functional or not. However, it is also possible for the functionality of the electrode arrangement to be assessed in a more complex way, in particular with regard to determining the momentary plasma power and possibly the selection of an action depending on the determined momentary plasma power.

In the context of the method, the plasma power is preferably captured as a power parameter or with respect to the at least one power parameter.

According to a further development of the invention, it is provided that the action is selected from a group consisting of an output of an "OK" signal, an output of a "action needed" signal, an output of a "not OK" signal, a notification to an operator of the electrode arrangement of the—in particular, momentary—plasma power, an adaptation of an operating period or treatment duration to the comparison result, termination of the operation of the electrode arrangement, and continuation of the operation of the electrode arrangement without further measures, in particular without outputting a signal or a message. An "OK" signal is also referred to as a green signal, an "action needed" signal is also referred to below as a yellow alarm, and a "not OK" signal is also referred to below as a red alarm. A green signal indicates that the electrode arrangement is working as intended.

The green signal can in particular be output if the at least one power parameter deviates from the predetermined target parameter value by less than a first predetermined limit value, for example by less than 15%. A yellow alarm informs an operator of the electrode arrangement that the electrode arrangement should be checked, wherein further steps may optionally be necessary, for example cleaning the electrode arrangement, cleaning contacts, or other such measures. Such a yellow alarm is preferably output when the deviation of the at least one power parameter from the at least one predetermined target parameter value is greater than the first predetermined limit value, and is less than a second predetermined limit value, wherein the second predetermined limit value is greater than the first predetermined limit. The second predetermined limit value can correspond, for example, to a deviation of 30% from the predetermined target parameter value. The yellow alarm can also be output if the deviation of the at least one power parameter from the at least one predetermined target parameter value is equal to the first predetermined limit value. A red alarm can in particular be output if further operation of the electrode arrangement is no longer useful due to insufficient functionality, or is dangerous either for the electrode arrangement itself, for the subsequent user of an item treated with the plasma (for example, in drinking water treatment), for the operator, or for a person treated with the electrode arrangement. The red alarm can in particular be output if the at least one power parameter deviates from the at least one predetermined target parameter value by the second predetermined limit value or by more than the second predetermined limit value.

According to one embodiment of the method, the at least one predetermined target parameter value can be a target value, in which case the power parameter is compared with the—in particular, exactly one—target value, and the functionality of the electrode arrangement is assessed on the basis of the comparison result. In particular, a deviation from the target value both upwards and downwards, at least when certain limit values defined relative to the target value are exceeded, is an indication of a deficient functionality of the electrode arrangement.

According to another embodiment of the method, it is possible for the at least one predetermined target parameter value to be a minimum value. In this case, the power parameter is compared with the minimum value in such a way as to provide a verification of whether the power parameter is greater or less than the minimum value. The electrode arrangement is functional when the power parameter is greater than or equal to the minimum value, and the electrode arrangement is not functional when the power parameter is smaller than the minimum value. A range for a yellow alarm can also be defined, wherein this then extends, starting from the minimum value, up to a predetermined limit value which is less than the minimum value by a predetermined amount or a predetermined factor. The range for the red alarm then extends, starting from the predetermined limit value, towards lesser values, wherein the range for the yellow alarm is found between the predetermined limit value and the minimum value. In this case, the range for the green signal is above the minimum value.

In a corresponding—but simply opposite—way, in a further embodiment of the functional verification, the target parameter value can be defined as the maximum value. The electrode arrangement is not functional if the power parameter assumes values above the maximum value, wherein the electrode arrangement is functional when the power parameter assumes values below or up to the maximum value. The range of the green signal then extends from smaller values, in particular from zero, up to the maximum value, wherein the range of the yellow alarm extends, starting from the maximum value, to a predetermined limit value, which is greater than the predetermined limit value by a predetermined amount or a predetermined factor. The range of the red alarm then extends from the predetermined limit value to higher values.

In a further embodiment of the method, it is possible that two predetermined target parameter values are provided, and the at least one power parameter is compared to these. The two predetermined target parameter values define a value band or limits of a value range, wherein the electrode arrangement is assessed as being functional within this value band or value range. In particular, a first predetermined target parameter value is defined as the minimum value of the value band or value range, and a second, greater target parameter value is defined as the maximum value of the value band or value range. The ranges for the yellow alarm are then each assigned to the maximum value on the one hand and the minimum value on the other hand, in the same way as was explained above for the minimum value and the maximum value.

Alternatively, it is also possible that a range for a yellow alarm does not—as explained above—extend in the direction of the range for the red alarm, starting from the predetermined target parameter value, but rather that it extends into the range of the green signal. In this case, for example, the predetermined limit value assigned to the minimum value can be greater than the minimum value, wherein the predetermined limit value assigned to the maximum value can be less than the maximum value. Alternatively, it is also possible to define a yellow alarm area in such a way that it includes, preferably symmetrically, the predetermined target parameter value.

The at least one predetermined target parameter value is preferably selected as a function of a desired operating mode of the electrode arrangement, in particular as a function of a desired plasma chemistry, especially a desired concentration of certain active species in the plasma. For example, it is possible that different target parameter values, in particular a permissible value range or a permissible value band, are specified on the one hand for the case that the generated non-thermal plasma needs to substantially contain oxygen species, for example ozone (oxygen mode), or the case that the non-thermal plasma should substantially contain nitrogen species, in particular nitrogen oxides (nitrogen mode). It is also possible to choose an intermediate range between these operating modes. The plasma chemistry depends heavily on the selected plasma power and can therefore be specified by this. In this respect, the functionality of the electrode arrangement must also be tested with respect to the plasma power according to the selected operating mode.

The signals described here can be output as light signals, for example. In particular, it is possible for the green signal to be output as a green glowing light, the yellow alarm as a yellow glowing light, and the red alarm as a red glowing light. In particular, light-emitting diodes can be used to output the light signals.

The signals and/or notifications can, however, alternatively or additionally also be output in text form, in particular in a display, as acoustic signals or notifications, by vibration, or in another suitable manner.

A communication of the particular momentary plasma power to the operator enables the operator to estimate a treatment outcome of the electrode arrangement for a specific treatment duration and, if necessary, to adapt the treatment duration to the momentary plasma power. If, for example, the electrode arrangement has a momentary plasma power that is reduced compared to a nominal plasma power, the operator can extend the duration of treatment in a suitable manner in order to apply a specific plasma dose. Such an adaptation of the treatment duration can, however, preferably also take place automatically, in particular according to the comparison result. The operator is preferably informed about the automatically modified duration of treatment, or the operator is required to operate the electrode arrangement until its automatic termination of operation, in which case the modified treatment duration is taken into account essentially automatically. In this case, the treatment duration preferably corresponds to an operating duration of the electrode arrangement, since it is preferably only operated during a treatment that is actually carried out. Treatment then begins, in particular, with the beginning of operation of the electrode arrangement, and ends with the termination of operation of the electrode arrangement.

The operation of the electrode arrangement can in particular be ended or blocked if further operation of the same no longer makes sense or is dangerous for the electrode arrangement itself, the operator or a person being treated with the electrode arrangement. In particular, the operation of the electrode arrangement can be terminated or blocked at the same time that a red alarm is output.

If an undiminished functionality of the electrode arrangement is determined, its operation is preferably permitted or continued. In particular, the operation of the electrode arrangement can be permitted or continued at the same time that a green signal is output, in particular if the functional verification is carried out when the electrode arrangement is put into operation.

According to a further development of the invention, it is provided that the method is carried out immediately after the electrode arrangement has been put into operation—but preferably before it is used. In particular, it is possible for the functional verification to be carried out—in each case, anew—immediately after the electrode arrangement has been put into operation, preferably automatically. In this way, the electrode arrangement can be checked directly at the time it is put into operation, with the operator of the electrode arrangement preferably being given feedback as to whether the electrode arrangement is functional. In this way, before the actual use of the electrode arrangement, in particular before treating a surface or person with the electrode arrangement, it can always be determined whether the electrode arrangement is functional, wherein optionally the actual use of the electrode arrangement does not take place, and the same is checked, cleaned or sent to repair instead. On the one hand, this has the advantage that the operator is informed without delay about problems with the electrode arrangement, thereby preventing inadequate treatment or, possibly, a treatment which is not performed, without this being recognized, wherein measures can be taken directly to maintain or ensure the functionality of the electrode arrangement. Knowing whether the electrode arrangement is functional immediately at the moment when it is put into operation is also advantageous for any treatment protocols which must be arranged.

The method is preferably carried out exclusively before an application, in particular not during an application of the electrode arrangement. It therefore serves in particular as a preliminary functional test before actual use.

According to a development of the invention, it is provided that the at least one predetermined target parameter value is prespecified as a constant. This can be the case in particular when external conditions under which the electrode arrangement is verified are always at least approximately identical and/or when the at least one predetermined target parameter value is sufficiently insensitive to varying external conditions. In this respect, a power parameter is preferably used which varies at most to a small extent with external conditions of the electrode arrangement. The power parameter is particularly preferably selected such that its relationship to the actual plasma power of the electrode arrangement depends only to a small extent, and preferably not at all, on external conditions such as, in particular, temperature, humidity, aging effects such as corrosion, oxidation, deposits and the like. In this way it can be ensured that the power parameter in any case only depends on the plasma power of the electrode arrangement and is therefore always exclusively characteristic of the plasma power of the electrode arrangement.

Alternatively, it is possible that the at least one predetermined target parameter value is stored as a function of at least one application parameter of the electrode arrangement, wherein it can be called up or activated in particular as a function of the at least one application parameter. The at least one predetermined target parameter value is preferably stored with a dependence on the at least one application parameter in a characteristic map, from which it can be read according to the at least one application parameter. This is particularly useful if the conditions of use of the electrode arrangement, and thus a value of the at least one application parameter, can change over time. The at least one application parameter is preferably selected from a group consisting of an ambient temperature of the electrode arrangement and a relative humidity in an environment of the electrode arrangement. This is particularly relevant when treating moist surfaces or moist or wet environments, for example for wound treatment or water treatment. It can preferably be sufficient in this case to store two different values for the at least one predetermined target parameter value as a function of the relative humidity—for example, a first value for a relative humidity of 80% or more than 80%, and a second value for a relative humidity of less than 80%.

It is possible for the at least one application parameter to be measured by the electrode arrangement or a plasma source having the electrode arrangement. In this way, current, precise values of the usage parameter can always be obtained directly. Alternatively or additionally, it is possible that the at least one application parameter is obtained by the electrode arrangement or the plasma source, in particular from an external source. For example, it is possible for the at least one application parameter to be downloaded from a service provider or computer, obtained from a network, or input by the operator of the electrode arrangement via a suitable interface.

The plasma is preferably generated in ambient air by the electrode arrangement. The electrode arrangement is therefore not supplied with a separate carrier gas for generating the plasma. The operation of the electrode arrangement is therefore also influenced in a particular way by the ambient temperature and/or relative humidity in the proximity of the electrode arrangement.

The electrode arrangement is preferably operated with alternating voltage, in particular with a frequency of at least 2 kHz to at most 100 kHz. The electrode arrangement is preferably operated at a voltage of a few kilovolts, the voltage preferably being selected from at least 1 $kV_{pp}$ to at most 5 $kV_{pp}$, preferably 3.5 $kV_{pp}$.

According to a development of the invention, it is provided that the electrode arrangement is heated for the determination of the power parameter. For this purpose, the electrode arrangement is particularly preferably heated to a temperature of at least 50° C. In this way, it is possible to remove any moisture deposited on the surface of the electrode arrangement, which may otherwise negatively impact the measurement.

In particular, the plasma power can be determined in various ways:

A preferred option is Fourier (or power spectrum) analysis, where only the power in the high-frequency part of the spectrum is determined. Since the plasma discharges generate many small "spikes" (essentially like delta functions), the plasma power can be measured in the high frequency range.

In another preferred measurement method, the plasma power is described by the area of a Lissajous figure which is generated by a phase space diagram of a control voltage, which is defined as the voltage that is applied to the electrode arrangement for plasma generation by means of a high-voltage source, plotted against a plasma voltage, which is defined as the voltage that is actually applied across the electrode arrangement during its operation, wherein the control voltage is accordingly the unmodified operating voltage of the plasma device and the plasma voltage is the voltage which is modified/deformed by plasma discharges, phase-shifted relative to the control voltage, and which drops across the electrode arrangement. In this case, it is preferred not to take into account the individual micro-discharges in the voltage curve, but rather a suitable averaging. The phase space diagram creates a closed curve around an enclosed area. This enclosed area contains information about the deformation of the control voltage caused by the micro-discharges, as well as the phase shift between the control voltage and the plasma voltage, and thus constitutes a measure of the plasma power.

In practice, for various reasons, it is not always possible to use this phase space diagram and/or to measure the voltage curves directly. Control voltage then means: applied high voltage or voltage which corresponds to the applied high voltage in form, phase and amplitude; and instead of the plasma voltage, a proxy voltage is measured, which drops across an electronic proxy structure connected in series with the electrode arrangement—in particular also referred to as "proxy measurement"—wherein the proxy voltage is generated by effects (deformation and phase shift) caused by the micro-discharges (which contain the actual plasma power). The enclosed area of this "proxy measurement" or the proxy voltage in itself also describes the plasma power.

There are various ways to carry out such a "proxy measurement" that maps the plasma power:

1. The phase space curve of the control voltage is plotted against the proxy voltage, and the integral of the area enclosed in this way is taken.
2. The proxy voltage is measured at a specified point in time in the sine curve of the control voltage. The positioning of this point in time of the control voltage is optimally chosen such that the maximum width and/or height of the Lissajous figure is targeted. This position is optimally in the area of the greatest temporal gradient and/or phase difference between the control voltage and the proxy voltage.

An easily definable point for this measurement is the zero crossing of the control voltage. The proxy voltage at this point is close to the maximum width or height of the Lissajous figure. The proxy voltage detected in this way is an easily measurable parameter that represents the plasma power. For this purpose, a suitable choice of a proportionality factor is required: this can be determined in particular by comparison with the enclosed area of the Lissajous figure.

Because of the "discretization" of the measurement, a micro-discharge may or may not be found by chance with such a singular measurement. For this reason, a sufficient number of measurements—preferably 256 measurements—is preferably averaged in order to obtain a reliable result for the plasma power.

According to a further development of the invention, it is provided that the at least one power parameter is detected in an electronic proxy structure connected in series with the electrode arrangement, in particular an electronic proxy structure of the plasma device, in particular as a proxy measurement. This enables a simple measurement of the power parameter, which can be carried out in particular even with a small, portable, hand-held device, and which is nevertheless characteristic of the plasma power of the electrode arrangement.

An electronic proxy structure is understood here to mean in particular an electronic component or a plurality of electronic components electrically connected directly or indirectly and interacting with each other, which is particularly suitable for allowing the performance of a proxy measurement to determine the at least one power parameter and ultimately the plasma performance.

According to a further development of the invention, it is provided that a capacitor is used as the electronic proxy structure. In this context, a capacitor is generally understood to mean an electronic structure that at least behaves capacitively, preferably substantially capacitively, preferably exclusively capacitively. At least one capacitor or a capacitor arrangement, particularly preferably precisely one capacitor, is particularly preferably used as the electronic proxy structure. It has been found that the use of a capacitor as an electronic proxy structure for the functional verification proposed here produces a particularly reliable conclusion about the actual plasma power of the electrode arrangement.

The capacitance of the electronic proxy structure—hereinafter referred to as proxy capacitance—is preferably greater, in particular very much greater, preferably by a factor of at least 500 to at most 2000, preferably of at least 750 to at most 1500, preferably of 1000, greater than the capacitance of the electrode arrangement during the plasma operation—hereinafter referred to as the arrangement capacitance.

The voltage $V_{proxy}$ is related to the plasma voltage $V_{plasma}$ in the following way:

$$V_{proxy} = \frac{c_a}{c_a + c_p} V_{plasma}, \quad (1)$$

where $C_p$ is the proxy capacitance and $C_a$ is the arrangement capacitance.

This is explained in more detail using a preferred embodiment:

(Beginning of the preferred embodiment.) The arrangement capacitance is preferably proportional to a total edge length L (sum of all edge lengths) of a structured electrode of the electrode arrangement, at the edges of which the plasma is generated, and is found as:

$$C_a = c_L \cdot L \quad (2)$$

with the proportionality factor $c_L$.

The arrangement capacitance is, for example, 109 pF, and the plasma voltage is 3.5 $kV_{pp}$ (peak to peak). Furthermore, the total edge length L is 72 cm. This means that $c_L = C_a/L = 1.51$—such a value is typical for SMD electrode arrangements, where $c_L$ is in the range $1 < c_L < 2$.

For metrological reasons, a value for the proxy voltage of roughly 3 to 5 $V_{pp}$ is desirable. This results in a scaling (where $C_p >> C_a$):

$$C_p = \frac{c_L \cdot L}{V_{proxy}} V_{plasma}. \quad (3)$$

The value of the plasma voltage is known from the control voltage (typically several kV), as is the desired proxy voltage. $C_p$ can be determined for an electrode configuration, which is substantially specified by the total edge length L, and the type of electrode (for example, SMD—which defines $c_L$).

For a preferred electrode arrangement, equation (3) yields a reference value for the proxy capacitance of $C_p = 100$ nF (with $V_{proxy} = 3.5$ $V_{pp}$ and $V_{plasma} = 3.5$ $kV_{pp}$. (End of the preferred embodiment.)

According to a further development of the invention, it is provided that at least one value of the proxy voltage is measured as the at least one power parameter at a specific phase angle of the control voltage, in particular when the control voltage crosses zero. A mean value PM of the proxy voltage at the determined phase angle of the control voltage, averaged over several, in particular a plurality of, periods of the control voltage, is preferably determined as the at least one power parameter:

$$PM = \frac{1}{n} \sum_{i=1}^{n} V_{proxy,i}(\varphi), \quad (4)$$

where in equation (4), $V_{proxy,i}(\varphi)$, the value of the proxy voltage at the fixed phase angle $\varphi$—in particular at the zero crossing—of the control voltage is in the period i, and where n is a number of the periods of the control voltage over which the averaging takes place. According to a preferred embodiment, n=256; according to another preferred embodiment, n can assume a different or greater value. If n=256, for a frequency of the control voltage of x kHz, the mean value of the proxy voltage measured continuously once in each period is calculated every 1/(4x) seconds if all measurements take place consecutively in successive periods. Especially with high frequencies, a measurement is only possible in certain periods (for example, every second or third period, etc.), or it is necessary to measure every 256 periods one after the other and then leave a gap of a certain number of periods. The corresponding procedure must of course be taken into account to determine the plasma dose.

An assignment of the power parameter to the actual plasma power is preferably stored in a control device for controlling the electrode arrangement, preferably as a simple factor or as a more complex, preferably at least injective, preferably bijective function that unambiguously assigns an actual plasma power to a measured value of the power parameter.

According to a development of the invention, it is provided that the power parameter is compared with a first, upper target parameter value and with a second, lower target parameter value. The first, upper target parameter value is greater than the second, lower target parameter value. The at least one action is selected depending on whether the power parameter value falls within a target parameter range delimited by the first target parameter value and the second target parameter value. The first target parameter value and the second target parameter value thus bound a target parameter range in which the power parameter is intended to fall; this means that the electrode arrangement is functioning properly if the power parameter falls within the target parameter range. If, on the other hand, the power parameter is lower than the second, lower target parameter value or greater than the first, upper target parameter value, the electrode arrangement is not functioning properly and can either not be used or can only be used to a limited extent. The at least one action can in particular also be selected depending on how far the power parameter is from the first, upper target parameter value or from the second, lower target parameter value—outside the target parameter range. In particular, it is possible to separate an area for a yellow alarm and an area for a red alarm by means of corresponding further limit values.

The first target parameter value takes into account an upper power limit for plasma generation, wherein this upper power limit can be exceeded, for example, by erosion of a dielectric of the electrode arrangement, deposition on the dielectric, leakage current formation or other similar effects that increase the power consumption of the electrode arrangement. The lower, second target parameter value takes into account a lower performance limit of the electrode arrangement, which can be exceeded, for example, through contamination, deposition and/or erosion of conductive components of an electrode of the electrode arrangement, or through other, similar effects that reduce the power consumption of the electrode arrangement.

Each electrode arrangement is preferably characterized as part of an initial test, wherein the first and second target parameter values are individually determined for each electrode arrangement and application task (e.g., oxygen, nitrogen or intermediate mode), and preferably stored in an electronic storage device assigned to the electrode arrangement, for example an RFID chip or the like. In this way, intra-individual manufacturing variations can be detected, and a functional range that is as precise as possible can be specified for the individual electrode arrangement and application task. These individual threshold values can then be transmitted for each electrode arrangement, in particular by reading the memory device, even when the electrode arrangement is replaced in an existing plasma source. The memory device, for example the RFID chip or another data carrier, is preferably connected to the electrode arrangement so that it can be carried along with it, and is arranged and/or exchanged together with it on the plasma source.

According to a development of the invention, it is provided that the electrode arrangement is operated for a predetermined period of time before the at least one power parameter is determined. In this way, it can be ensured that constant operating conditions and/or an equilibrium for the operation of the electrode arrangement has/have been established, such that the power parameter is also correctly captured.

According to a further development of the invention, it is provided that the comparison result and/or the at least one power parameter is/are logged in an electronic storage device for later retrieval. The electronic storage device can be integrated directly into a control device of the plasma source, or can also be provided externally for this purpose. In particular, it is possible for the logging to take place in an external service provider which is operatively connected to the control device via a wired or wireless data connection, for example WLAN and/or Bluetooth. Particularly preferably, the comparison result and/or the at least one power parameter is/are automatically logged, and/or particularly preferably is/are linked to at least one metadata item, for example a time stamp, information about a location of the use of the electrode arrangement, information about a purpose or a type of use of the electrode arrangement, information about certain parameters of the operation of the electrode arrangement, or the like. In this way, a logbook for the operation of the electrode arrangement can be created, so that its functionality and readiness for use, and/or its operation in general, can be traced over time.

It is preferably also possible to remotely monitor, read, and/or control the electrode arrangement via a wired or wireless active connection, in particular a radio connection, preferably WLAN and/or Bluetooth, particularly preferably via Internet access and/or via a smartphone app.

According to a development of the invention, it is provided that an electrode arrangement which is configured to generate surface micro-discharges in ambient air is tested. Such an electrode can be tested using the method proposed here. The plasma is generated over a planar area or along a line, in particular at the edges of a structured electrode of the electrode arrangement, directly in ambient air. A spacer is preferably assigned to the electrode arrangement in order to ensure a certain distance from a treatment surface. The spacer is preferably designed in such a manner that it encloses a volume with the treatment surface during operation of the electrode arrangement, such that the plasma is generated by the electrode arrangement in a closed volume.

According to a development of the invention, it is provided that an electrode arrangement is tested which has a first, in particular planar electrode and a second, preferably planar electrode. The electrode arrangement also has a dielectric, by means of which the first electrode and the second electrode are spaced from each other, wherein the first electrode and the second electrode are each in mechanical contact with the dielectric, on opposite sides of the dielectric as viewed in the stacking direction of the stack comprising the electrodes and the dielectric. In this case, they can in particular be arranged on opposite surfaces of the dielectric, or be at least partially embedded in the dielectric. Particularly preferably, the first electrode is arranged closely against a first side of the dielectric, and the second electrode is arranged closely against a second side of the dielectric opposite the first side, for example by vapor deposition, screen printing, physical or chemical vapor deposition, by applying or pressing, gluing, or in any other suitable way.

In this way, an electrode arrangement is created which is suitable for generating surface micro-discharges on one of the two electrodes on one side of the dielectric, in particular on the edges of this electrode, and thus generating a non-thermal plasma without the need to arrange a treatment surface between the electrodes and/or an electrode and the dielectric, and further without the treatment surface itself having to be connected in the circuit as a counter electrode. Furthermore, it is possible to generate the non-thermal plasma at least largely uniformly on the surface on which the surface micro-discharges are ignited, such that uniform and constant conditions and plasma parameters can be achieved over this surface.

The second electrode is preferably pushed or pressed against the second side of the dielectric, that is to say it is preferably in contact with the second side of the dielectric, in particular under bias or contact pressure. This enables a close and stable arrangement of the second electrode on the second side of the dielectric without an air gap, which is favorable for the efficiency and the plasma generation rate of the plasma source. At the same time, the electrode arrangement can be produced in a simple manner, in particular since the second electrode can be produced separately from the dielectric and then only has to be placed against it and subjected to a biasing load or pressing force. The second electrode is also very easy to replace.

It is possible that the first electrode is also pushed or pressed against the first side of the dielectric, in particular with a biasing load or pressing force. However, the first electrode is particularly preferably coated, in particular vapor-deposited, onto the dielectric.

The second electrode preferably has a periodic structure composed of a plurality of identical structural elements, and/or the second electrode has at least one structural element with at least one recess delimited by edges. The second electrode is accordingly designed as a structured electrode which has edges on which surface micro-discharges can be ignited.

The edges delimiting the recess preferably have an edge length within each recess of at least 0.5 mm to at most 10 mm, preferably of at least 1 mm to at most 8 mm, preferably of at least 2 mm to at most 7 mm, preferably of 5 mm with respect to each other.

Additionally or alternatively, it is preferably provided that the second electrode has a plurality of structural elements, wherein the individual structural elements are at a distance of at least 0.5 mm to at most 10 mm, preferably of at least 1 mm to at most 8 mm, preferably of at least 2 mm to at most 7 mm, preferably 5 mm, from each other.

The first electrode is preferably provided with an insulating layer and/or potting compound.

According to a further development of the invention, it is provided that, when the electrode arrangement is in operation, a high voltage, in particular an alternating voltage, preferably with an amplitude of at least 1 $kV_{pp}$ to at most 5 $kV_{pp}$, and/or with a frequency of at least 2 kHz to at most 100 kHz, is applied to the first electrode. The frequency is preferably selected in particular according to the properties of a high-voltage source which is used. The second electrode is preferably connected to ground.

During the operation of the electrode arrangement for treating a surface, the first electrode preferably faces away from the treatment surface, and the second electrode faces the treatment surface. In this case, the stacking direction of the stack of the electrode arrangement comprising the first electrode, the second electrode and the dielectric extends obliquely or transversely, preferably perpendicularly, to the treatment surface. This means that the electrical safety with respect to the treatment surface is particularly high, since it can only come into contact with the second, grounded electrode if used as intended.

At the same time, the second electrode is the one on which the surface micro-discharges are ignited and the plasma is thus generated; it can act directly on the treatment surface.

The method proposed here can be carried out in general for a large number of different, in particular flat or linear, electrode arrangements. In particular, it can be carried out for electrode arrangements which are constructed according to the principle of dielectric barrier discharge (DBD), the principle of surface micro discharge (SMD), and/or as a coated SMD electrode. The method is particularly suitable for electrode arrangements that are capacitively coupled.

However, the method is particularly preferably carried out for an electrode arrangement which is described in more detail below in connection with the plasma source proposed here:

The object is achieved in particular by creating a plasma source having an electrode arrangement for generating a non-thermal plasma, the electrode arrangement having a first electrode, a second electrode, and a dielectric by means of which the first electrode and the second electrode are spaced from each other. The first electrode is arranged on a first side of the dielectric, and the second electrode is arranged on a second side of the dielectric, opposite the first side. The plasma source also has a control device which is configured to control the electrode arrangement. The control device is also configured to carry out a method according to the invention or a method according to one of the embodiments described above. The advantages which have already been explained in the context of the method are particularly achieved with the plasma source.

The first electrode is preferably arranged close against the first side of the dielectric. Alternatively or additionally, the second electrode is preferably arranged close against the second side of the dielectric. It is also possible for at least one electrode selected from the first electrode and the second electrode to be embedded in the dielectric. Also, both electrodes can be embedded in the dielectric. However, it is also possible for at least one electrode, selected from the first electrode and the second electrode, to be pressed against the side of the dielectric to which it is assigned. The second electrode is particularly preferably pressed against the second side of the dielectric.

According to one embodiment of the plasma source, it is possible for the second electrode to have a material which is selected from a group consisting of stainless steel, titanium, tungsten, an electrically conductive plastic, and a conductive adhesive. The materials specified here for the second electrode have good electrical conductivity, and at the same time they are suitably hard for sputtering, and thus durable and stable over the long-term, and resistant to oxidation, in particular when exposed to ozone. As such, these materials are particularly suitable for long-term use, especially in the medical field and in particular for generating ozone, and they can also be furnished inexpensively.

The fact that the second electrode is pressed against the second side of the dielectric means in particular that in this case it is not embedded in the dielectric and is not materially bonded to the dielectric. Rather, the second electrode is preferably held against the second side of the dielectric under mechanical preload, in particular pressed against the second side of the dielectric, or pressed onto the second side of the dielectric. In this way, the electrode arrangement can be produced very easily and inexpensively, wherein air can be effectively displaced from a gap between the second electrode and the dielectric at the same time due to the preload force which presses the second electrode against the dielectric, such that the closest possible contact of the second electrode on the second side of the dielectric is achieved. In the event of damage, the second electrode can be exchanged very easily, since it can be detached from the dielectric easily and, in particular, in a non-destructive manner, in particular by relieving the mechanical preload. In particular, it is possible for the second electrode to be pushed against the second side of the dielectric by a biasing element or a pressing element.

The entire electrode arrangement is particularly preferably held together by preload forces, wherein it is possible for the electrode arrangement in particular to be pressed or compressed together.

It is preferably also possible for the first electrode to be coated, in particular vapor-deposited, onto the dielectric. Alternatively or additionally, it is possible for the second electrode to be coated onto the dielectric, in particular vapor-deposited.

The electrode arrangement is configured in particular to generate surface micro-discharges.

If a potential difference, in particular an alternating voltage, is applied to the two electrodes—that is, the first electrode and the second electrode—surface micro-discharges (SMD) form on an active surface of the electrode arrangement, in particular in the region of the second electrode, especially in the region of the edges of the second electrode, which in turn lead to the formation of a nonthermal plasma in the region of the active surface.

The first electrode and the second electrode are designed in particular as powered electrodes.

An electrically conductive plastic is understood to mean in particular intrinsically conductive polymers, which are also referred to as conductive polymers. These form plastics whose electrical conductivity is comparable to the electrical conductivity of metals. At the same time, such plastics are very light. Examples of such electrically conductive plastics are, for example, poly-3,4-ethylenedioxythiophene (PEDOT or PEDT), in particular in combination with polystyrene sulfonate (PSS) as counterion, polyacetylene, polyaniline, polyparaphenylene (PPP), polypyrrole (PPy) and doped polythiophene (PT).

A conductive adhesive is understood in particular to be an electrically conductive adhesive. This also combines low weight with good electrical conductivity and simple applicability.

The dielectric preferably has a material or consists of a material which is selected from a group consisting of Kapton, quartz, glass and ceramic, in particular aluminum oxide.

The dielectric preferably has a thickness of at least 0.05 mm to at most 0.8 mm, preferably of at least 0.1 mm to at most 0.75 mm, and particularly preferably 0.25 mm, as measured in the stacking direction of a stack formed by the first electrode, the dielectric and the second electrode.

The first electrode preferably has a thickness—measured in the stacking direction—of at least 1 µm to at most 100 µm, in particular a thickness of at least 2 µm to at most 6 µm, in particular a thickness of 4 sm.

The second electrode preferably has a thickness—measured in the stacking direction—of at least 5 µm to at most 1 mm, preferably a thickness of 0.5 mm.

The electrode arrangement can have a flat shape, and/or a curved shape. It is possible for the electrode arrangement to be rigid. The electrode arrangement can, however, preferably also be flexible, in particular bendable.

In a preferred embodiment, the first electrode has a surface area of 2 cm to 5 cm, preferably 3 cm, by 2 cm to 5 cm, preferably 3 cm, and is preferably square. The dielectric and the second electrode are preferably also square and/or designed with a surface area of 3 cm to 6 cm, preferably 4 cm, by 3 cm to 6 cm, preferably 4 cm. The first electrode is preferably arranged centrally relative to the arrangement made up of the dielectric and the second electrode. A specific embodiment of the electrode arrangement has a surface area of 3.4 cm by 3.4 cm for the first electrode.

If the area of the first electrode is smaller than the second electrode—that is, if the second electrode projects beyond the first electrode at the edge—the first electrode is preferably provided with an insulation layer that prevents microdischarges from occurring along the edge of the first electrode.

According to a further development of the invention, it is provided that the control device has an electronic proxy structure that can be or is connected in series with the electrode arrangement, wherein the at least one power parameter is captured by the control device on the electronic proxy structure. The electronic proxy structure is preferably the electronic proxy structure explained in connection with the method.

According to a development of the invention, it is provided that the electronic proxy structure is designed as a capacitor, in particular as a capacitor or capacitor arrangement.

According to a further development of the invention, it is provided that the second electrode has a periodic structure made up of a plurality of identical or different structural elements. The structural elements individually or in combination with each other form unit cells of the periodic structure. The second electrode is accordingly designed in particular as a structured electrode. The structural elements are electrically connected to each other, and in particular they can be set to the same potential. The structural elements can be designed essentially in one-dimension, for example as straight or curved or sinuous, linear or wave-shaped sub-electrodes, or they can be designed to be two-dimensional, for example as a two-dimensional, continuous structure such as a meander structure, or as polygons, in particular as a triangle, square, pentagon, hexagon or higher-sided polygon. The structural elements can also be designed as circles, ellipses or ovals. A plasma discharge forms in particular at the edges of the structural elements.

If the second electrode has a periodic structure made up of a plurality of identical structural elements, it is designed in particular to be scalable. This means that a generation rate of reactive species in a plasma generated by the electrode arrangement scales linearly with the flat or geometrically linear extent of the second electrode and in particular with the number of identical structural elements or the total edge length of the structural elements for the same specific power, with respect to a unit area of the electrode arrangement or to a unit edge length of the edges of the structural elements of the second electrode along which the plasma is generated.

This proves to be particularly favorable for tuning the electrical, chemical and/or microbial properties of the electrode arrangement.

According to a further development of the invention, it is provided that the second electrode has at least one structural element with at least one recess delimited by edges, wherein the edges delimiting the recess within each recess have an edge length of at least 0.5 mm to at most 10 mm, preferably of at least 1 mm to at most 8 mm, preferably of at least 2 mm to at most 7 mm, preferably of 2 mm or of 5 mm with respect to each other. Such a structural element can in particular be designed as a polygon, for example a triangle, a square, a pentagon, a hexagon, or a polygon with a higher number of corners. The edges of the polygon are preferably formed from conductive material of the second electrode, wherein no conductive material is formed within the recesses delimited by the edges—that is, in particular in the interior of the polygon. In this case, a plasma discharge forms along the edges of the structural element. It has been shown in this case that the electric fields emanating from two edges abutting each other in a corner of the polygon interfere with each other in the corner region, and particularly self-interference occurs here. This causes a reduction in the power of the electrode arrangement, in particular a reduction in the plasma generation rate, because losses arise. These losses are smaller in relation to the plasma power of the electrode arrangement when the structural elements are larger, which means in particular that the relative losses become smaller as the edge lengths of the structural elements become longer. In particular with the values given here and very preferably starting at an edge length of 2 mm, the power-reducing effect due to self-interference can be accepted or neglected.

The self-interference described here also stands in the way of freedom to make any desired refinements, and thus an increase in the area power of the electrode arrangement. If, for example, the second electrode has a periodic structure made up of a plurality of identical structural elements, each of which has a recess delimited by edges, theoretically, for example, the generation rate could be doubled with the same total area of the second electrode if a characteristic length of the structural elements, for example the edge length of a square structural element, would be halved. As a result, the number of structural elements on the entire, constant electrode surface could be quadrupled, as a result of which the overall length of the edges, that is to say the sum of the edge lengths of all structural elements, would be doubled. This would also double the generation rate if no self-interference occurred. However, the smaller the structural elements—that is, the shorter their edge lengths—the greater the power-reducing effects of the self-interference in the corners, such that the generation rate no longer scales linearly with the number of structural elements and the total edge length. There is thus an effective lower limit for the edge length of the individual structural elements, with suitable ranges for the edge lengths of the structural elements being specified above.

It has also been recognized that the self-interference occurs to a greater extent the smaller the angle between two edges of a structural element which meet in a corner. In the case of a triangle, for example an isosceles triangle in which the edges meet at an angle of less than 60°, the self-interference has a more negative effect on power than, for example, in the case of a square in which the edges meet at an angle of 90°. Correspondingly, the power-reducing effect of the self-interference in the corners decreases with the number of edges that a polygonal structural element has, or more generally with an increasing angle at which two edges of a structural element meet in a corner.

The value ranges specified above are optimal in particular for a square structural element, but can easily be used for other, polygonal structural elements. However, the more edges a structural element has, or the greater the angle of two edges meeting each other in a corner relative to each other, the smaller the values can in principle be selected to be.

Alternatively or additionally, it is preferably provided that the second electrode has a plurality of structural elements, the individual structural elements being at a distance of at least 0.5 mm to at most 10 mm, preferably of at least 1 mm to at most 8 mm, preferably of 5 mm, from each other.

This distance between the individual structural elements is also relevant because, in particular, smaller distances, that is to say finer grids, can lead to efficiency losses due to interference effects.

The second electrode particularly preferably has a periodic grid of square structural elements, the edges of a square structural element having a width of 0.5 mm—measured perpendicular to its extension—and a recess in such a square structural element preferably having an inner edge length of 5 mm.

According to a preferred embodiment, the electrode arrangement is planar. It is also possible, however, for the electrode arrangement to be designed in the shape of a semi-cylinder, wherein the second electrode preferably has structural elements, the size of which increases from a center—i.e., an apex of the semi-cylinder—outwards. As a result, the generated plasma can be concentrated in the central region, that is to say at the apex or extreme of the semicylindrical electrode arrangement, while there is a lower plasma power or generation rate in the edge areas.

A spherical electrode arrangement or a hemispherical electrode arrangement is also conceivable. In this case, the second electrode preferably has a soccer ball-like structure that is formed from alternating pentagons and hexagons.

The second electrode can also be linear, straight, zigzag, curved, wavy, spiral, comb-like or meandering.

According to a development of the invention, it is provided that the first electrode comprises copper and/or tin. The first electrode consists alternatively of copper or a copper alloy and/or of tin or a tin alloy. The first electrode particularly preferably has a first layer made of copper or a copper alloy, and a second layer made of tin or a tin alloy arranged on the first layer. The copper layer is preferably facing the dielectric, the tin-containing layer being arranged on the copper-containing layer and facing away from the dielectric. The tin-containing layer serves in particular for better contactability of the first electrode. In contrast, the layer comprising copper has a particularly high electrical conductivity and, in particular, a higher electrical conductivity than tin. The layer comprising copper preferably has a thickness of 3 µm, measured in the stacking direction. Alternatively or in addition, the tin-containing layer preferably has a thickness of 1 µm, measured in the stacking direction.

According to a further development of the invention, it is provided that the dielectric and the second electrode protrude beyond the first electrode on all sides—viewed perpendicular to the stacking direction. This configuration has, in particular, mechanical advantages in the fact that the second electrode is firmly pressed or pushed against the dielectric. It may be problematic, however, that regions of the second electrode that protrude beyond the edges of the first electrode can experience field increases in the electric field, as a result of which undesired discharge paths are formed—for example, through leakage currents or corona discharges. This in turn reduces the efficiency of the electrode arrangement.

Alternatively, it is possible for the first electrode and the dielectric to protrude beyond the second electrode on all sides—viewed perpendicular to the stacking direction. In this case, the previously described field increases can be avoided at least to a large extent, in particular except for a contacting area in which the second electrode is contacted, such that the efficiency of the electrode arrangement is high.

Alternatively, it is also possible for the dielectric to protrude beyond the first electrode and the second electrode on all sides—viewed perpendicular to the stacking direction. In this case, a possible discharge path from the first electrode to the second electrode or vice versa over the surface of the dielectric is particularly long, so that leakage currents and other parasitic discharges, for example corona discharges, are effectively prevented.

According to a development of the invention, it is provided that the first electrode is coated with an electrical insulating layer and/or encapsulated with a potting compound. In this way, in particular the electrode to which a voltage is properly applied can be insulated and, in particular, enclosed, which increases the electrical safety of the electrode arrangement. The insulating layer preferably has an insulating varnish, in particular a two-component insulating varnish. This can be sprayed or painted on the first electrode, or applied in another suitable manner. The insulating layer and/or potting compound also serves to prevent leakage currents. In particular, sprayable insulating varnishes can be used to form the insulating layer.

In the context of the method, preferably an electrode arrangement of a plasma source is tested which is configured to generate a non-thermal plasma and which comprises an electrode arrangement according to one of the examples described above. In addition to the electrode arrangement, the plasma source preferably has a control device for controlling the electrode arrangement, in particular for energizing it, and an electronic storage device, namely in particular the electronic storage device assigned to the electrode arrangement already described above. The control device is configured in particular to carry out a method according to any one of the embodiments described above.

The plasma source is preferably designed as a hand-held device which can be held and carried by a user, preferably with one hand. The plasma source can in particular have a size allowing it to be operated and carried with one hand, for example the size of a telephone receiver or a shower head.

The plasma source also preferably has means to communicate with a user, these means preferably being selected from a group consisting of acoustic communication means, in particular a loudspeaker, optical communication means, in particular signal lights, preferably light-emitting diodes, a display means for displaying graphics and/or texts, in particular at least one display, and vibration means for generating a vibration of the plasma source.

The plasma source is preferably designed to be battery-operated or accumulator-operated, and as such can be operated wirelessly, and in particular without contact with a stationary, larger device. Since the plasma is generated in ambient air, the plasma source preferably also does not have a gas supply for supplying a carrier gas.

The plasma source can, however, also be designed as a larger, stationary and/or wired device.

In the following, fundamental considerations regarding the previously described method for testing an electrode arrangement for generating a non-thermal plasma are explained in more detail:

Flat or linear electrode arrangements (for example, DBD, SMD, coated SMD, regardless of their geometry) vary in their plasma power depending on environmental conditions. This applies in particular to the air humidity, which can have a strong influence, in particular on the dielectric, depending on the materials used. This is partly due to the chemical conditions of the air (for example, probabilities of excitation, dissociation, ionization), which are mainly represented by the varying humidity, but also by condensation on the electrodes and absorption and diffusion into the dielectric material. The latter can be reduced before each use by, for example, "heating up" the electrode arrangement—but the former cannot be compensated for without knowledge of the environmental conditions. In addition, the electrode arrangement can age and become dirty through prolonged use, which impairs functionality. "Aging effects" include, for example, corrosion, deposits, and surface changes, which can occur with prolonged use and can lead to an impairment of power.

In most cases, the functionality of the electrode arrangement is not assessed by a simple yes/no decision which merely determines whether current is flowing. For example, for hygiene, surface treatment, textile treatment, water treatment, treatment of food, seeds, skin diseases and wounds, it is crucial that the plasma dose is sufficient for any given application, in order to inactivate pathogens (bacteria, viruses, spores) to the desired degree. "Plasma dose" is the product of the plasma generation rate (plasma power) multiplied by time. The plasma chemistry, which is controllable and thus defines the field of application, is also important. The plasma chemistry can also be dependent on the plasma power (for example, in air, either oxygen or nitrogen chemistry can be selected as dominant, or an intermediate range or a sequential variable treatment).

Procedure:

In general, the typical task is as follows:

The predominant property of the plasma source is the inactivation of pathogens—primarily bacteria, and/or the inactivation of allergens, odor molecules or other undesirable or dangerous molecules (decontamination)—up to a required log reduction in a predetermined time t.

Example of Bacterial Inactivation in a Given Time:
1. Appropriate bacterial tests must be carried out for the desired treatment time. These define the plasma power that is preset on the device.
2. The decisive measured variable for this is the plasma power PL—that is, how much energy is put into the generation of a non-thermal, cold atmospheric plasma per second?

The plasma is generated in the SMD electrode in millions of micro-discharges, which can be seen in the current curve as narrow "spikes"—each spike with a typical duration of a few tens of nanoseconds. This high-frequency component cannot be measured directly for a small hand-held device, for example; the effort is too great. For a larger system, the effort is also high, but more feasible—unless a simpler, reliable process exists.

3. A measured variable must therefore be found which can be found by a simple measurement that allows a direct conclusion to be drawn about the plasma power PL—a power parameter PM. There does not have to be a linear relationship between the power parameter PM and the plasma power PL; rather, an unambiguous, preferably bijective, relationship between these quantities is sufficient. However, a linear relationship represents a particularly simple embodiment, which is why it is assumed as an example in this case.

This output parameter PM should apply to all environmental conditions—that is, PM/PL should ideally be constant, regardless of temperature and humidity. PM can then be used to clearly identify the plasma power PL of the plasma source in every application—by means of a simple first "scaling factor" S1=PL/PM.

4. The electrode arrangement can have "aging effects" that do not affect the effectiveness, but can change the plasma power.

The ratio S1=PL/PM should ideally also be constant for electrode arrangements with signs of aging, wherein this ratio is always the same in the optimal case, regardless of the age of the electrode arrangement. However, this is not to be expected, because the electrode arrangements can change (for example, through corrosion, oxidation, deposits). Therefore, aging effects must be investigated in long-term tests, and if necessary the electrode arrangement must be replaced after a certain number of uses.

5. If the measurement takes place under different environmental conditions than the final operating conditions (not uncommon for a function test prior to application), the scaling from the environmental to the operating conditions must also be determined experimentally.

This is the case, for example, when a function test is carried out in the normal room environment, but the application takes place in a damp, closed volume (this corresponds, for example, to water treatment or possibly wound treatment). For this purpose, an additional second scaling factor (S2) is required, which is determined experimentally. The scaling from the "proxy measurement" of the power parameter PM to the final field of application is then given as the overall scaling factor S from the product of S1×S2=S.

6. The functionality test of the electrode arrangement can generally also be carried out under environmental conditions (temperature, relative humidity) that are not known.

So that the scaling to the field of application can still be used, it is important that the PL/PM ratio does not show any great variability with air humidity. In addition, it is advisable to determine a "standard range" for air humidity (in which the functionality will be checked, with a high degree of probability) and to carry out the scaling based on this.

7. Before use, the electrode arrangement is optionally first "warmed up" in order to alleviate storage effects (for example, due to condensation). The power parameter PM is then measured—under the prevailing (only approximately-known, or even unknown) environmental conditions.

The scaling factor S is applied to this measurement in order to obtain the calculated proxy plasma power under operating conditions. The intra-individual and inter-individual variation in the electrode arrangements must be taken into account as the "bandwidth" of the scaling factor.

8. A further complication: the electrode can be partially contaminated, such that the plasma power is reduced compared to a clean electrode.

It must be ensured that the values PM and PL are linked in the same way—that is, that S1 is ideally independent of the degree of contamination. The same applies to the second scaling factor S2. These relations must also be verified experimentally.

9. In the present case (especially for medical applications or water treatment), there is a further complication. The actual "measured variable" is not the plasma power—it is the bactericidal effect of the plasma, as noted at the outset. This is described by the integrated plasma dose in a preset operating mode. The duration of use, which exceeds the required minimum dose with an additional safety factor, is predetermined by appropriate tests and should always remain the same. This means that the "plasma dose" is only defined by the plasma power in the field of application, which can be determined using the above steps.

In order to guarantee a successful treatment, a lower threshold value PSU for the plasma power in the application must be determined experimentally. The threshold value for PM captured in the functionality test is then PU=PSU/S. If the plasma power PL is below the threshold value PSU, the electrode arrangement does not function well enough to achieve the required effect (for example, 3-4 log effective bactericidal reduction).

If the overall scaling factor S and the threshold value PSU have been chosen with sufficient care so that all manufacturing tolerances and expected environmental changes related to the (unknown) environmental conditions are included in the function test, the value PM>PU determined in this way guarantees that the plasma power is sufficient to achieve the required aim.

The first condition for positive functionality is therefore: PM>PU, where the lower threshold PU=PSU/S.

A second condition for positive functionality is specified by an upper threshold value, PSO, which must not be exceeded. Various disturbances (for example, age-related erosion of the dielectric, deposition of conductive erosion products on the dielectric, formation of leakage currents, etc.) can increase the plasma power above the normal operating value. In principle, the electrode arrangement is then still operational, but there are two important changes that must be taken into account:

A. The electrode arrangement is damaged and/or modified and therefore no longer comparable with the electrode arrangement that was used as a reference measurement (for example, in preliminary tests, in the laboratory or in preclinical studies);

B. The electrode arrangement could change from the oxygen mode to the nitrogen mode (if the power is sufficiently increased). This also changes the bactericidal effect and is not compatible with the preliminary tests, laboratory measurements or preclinical studies.

The second condition for positive functionality is therefore:

PM<PO, where the upper threshold PO=PSO/S.

In order to capture this logical chain, and to use it to generate safe operating parameters/threshold values "PSU and PSM" for all environmental conditions, a great number of measurements are necessary.

The plasma power PL must be measured independently, with the inherent corresponding difficulty, and both PL and PM must be determined and compared for all relevant environmental conditions. This has to be repeated for different degrees of contamination and aging of the electrode arrangement. All parameters generated in this way must be correlated with their bactericidal BE effect using bacterial studies. With all of these data sets in hand, the acceptable threshold value PS can be determined.

So that intra-individual fluctuations (for example, due to manufacturing tolerances) are also incorporated, these measurements must be carried out for a representative set of electrode arrangements, and the fluctuations must be taken into account (typically to 3a).

Examples: The required number of measurements (PM and PL at 3 temperature values with 7 humidity values each, plus 3 bacterial measurements and controls each) for 4 degrees of contamination—results in approx. 700 measured values per device—that is, more than 7,000 measurements for the required safety statistics!

The threshold value for the plasma power which is required to produce the desired bactericidal effect in the prespecified treatment duration of 1 minute is determined from a series of such measurements.

For a preferred electrode arrangement, the threshold value was determined to be 1 watt.

The degree of contamination can be important in this case. A certain exemplary embodiment of the electrode arrangement still functions when the contamination is more than 50%. Only once 80% contamination is reached is the bactericidal effect no longer noticeable.

It should also be mentioned that every new electrode arrangement has to be tested with a similar effort in order to create a reliable function test that applies to all relevant environmental conditions.

Of course, every new plasma source (electrode arrangement, high voltage source, and control device) must be tested in pre-clinical and in clinical studies for safety aspects in accordance with the specifications.

The invention is explained in more detail below with reference to the drawings, wherein:

FIG. 1 shows a schematic illustration of an embodiment of a method for testing an electrode arrangement for generating a non-thermal plasma, in the form of a flow chart. In this case, in a first step S1, the electrode arrangement is put into operation, wherein in particular a plasma source having the electrode arrangement is switched on.

Figure 1:
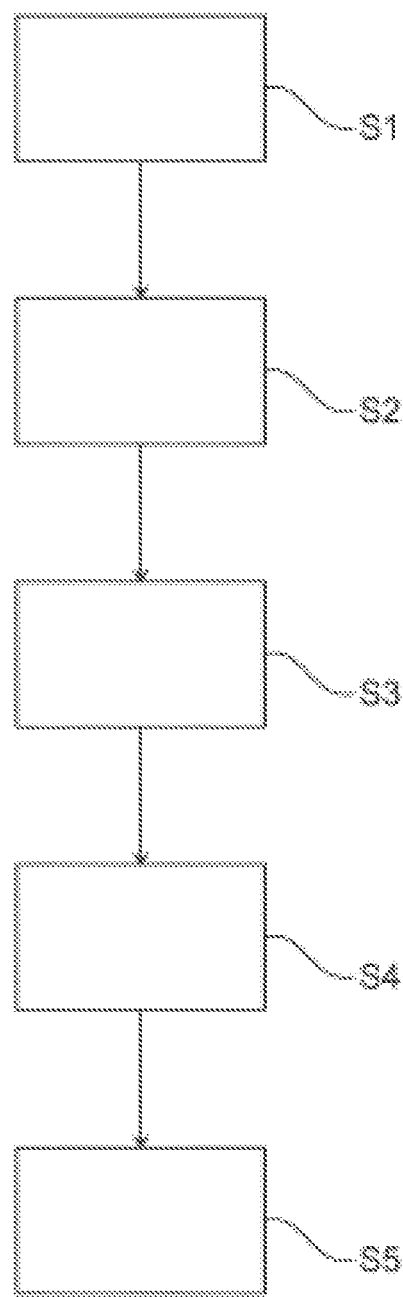
FIG. 1 is a schematic illustration of an embodiment of a method for testing an electrode arrangement, in the form of a flow chart.

In a second step S2, at least one power parameter is determined which characterizes a plasma power of the electrode arrangement.

In a third step S3, the at least one power parameter is compared with at least one predetermined target parameter value, and a comparison result is obtained.

In a fourth step S4, the functionality of the electrode arrangement is assessed on the basis of the comparison result.

In a fifth step S5, an action is preferably selected according to the comparison result. This action preferably includes—according to the comparison result—the output of an "OK" signal, the output of an "action needed" signal, the output of a "not OK" signal, notification of an operator of the electrode arrangement of a current plasma power, adaptation of an operating time of the electrode arrangement to the comparison result, termination of the operation of the electrode arrangement, or a continuation of the operation of the electrode arrangement without further measures, in particular without a signal or message output. The signal output can take place in particular in the form of light signals or luminous signals, for example the activation of a green, yellow or red light, in particular an LED. Alternatively or additionally, a text or a graphic symbol can be shown in a display. An acoustic output of a message or warning is also possible, as is the output of a message or warning by generating a targeted vibration of the electrode arrangement, in particular the plasma source, which has the electrode arrangement. For the selection of the action, predetermined ranges are preferably defined for the agreement or deviation of the at least one power parameter with/from the at least one predetermined target parameter value, and the action is selected according to which of the predetermined ranges the comparison result falls into.

The method is preferably carried out immediately after start-up, particularly preferably after each start-up of the electrode arrangement.

The at least one predetermined target parameter value is preferably specified as a constant. Alternatively, it is possible that the at least one predetermined target parameter value is selected according to at least one application parameter of the electrode arrangement, wherein it is possible in particular to store it in the form of a mathematical relationship, a characteristic curve or a characteristic field. The at least one application parameter preferably includes an ambient temperature of the electrode arrangement and/or a relative humidity in an environment, in particular an immediate environment, very particularly a treatment environment of the electrode arrangement—that is, an environment in which a treatment is carried out, in particular a surface treatment, by means of the non-thermal plasma generated by the electrode arrangement. In particular, two different values can be stored for the at least one predetermined target parameter value according to the relative humidity—in particular, a first value for a humidity of less than 80% and a second value different from the first value for a relative humidity of more than 80%.

The plasma is generated by the electrode arrangement in particular in ambient air, such that the relative humidity in the vicinity of the electrode arrangement is relevant for the plasma generation.

The electrode arrangement is preferably heated at least in portions thereof, to determine the power parameter, it being possible in particular for it to be heated to a temperature of at least 50° C. In this way, moisture accumulated on the surface of the electrode arrangement, which could otherwise impair the measurement, can be removed.

The comparison result and/or the at least one power parameter is preferably logged in an electronic storage device for later retrieval. The comparison result and/or the at least one power parameter is/are preferably stored with at least one metadata item, in particular together with a place of use, a purpose of use, a time stamp, and/or further metadata, preferably automatically. These parameters can then be read and/or graphically displayed at a later point in time in order to monitor the operation of the electrode arrangement and to assess its functionality over time.

The electrode arrangement is preferably configured to generate surface micro-discharges in ambient air.

An electrode arrangement is preferably used which has a first electrode and a second electrode, wherein the first electrode and the second electrode are spaced apart from each other by a dielectric, and in particular are in mechanical contact with the dielectric on different sides of the dielectric. The first electrode and the second electrode are preferably planar. The second electrode is preferably designed as a structure electrode or structured electrode which has a plurality of edges at which surface micro-discharges can be ignited.

A high voltage, in particular an alternating voltage, is preferably applied to the first electrode, and the second electrode is connected to ground. When the electrode arrangement is used to treat a surface, the second electrode is preferably facing the treatment surface, which increases the electrical safety of the operation of the electrode arrangement.

Figure 2:
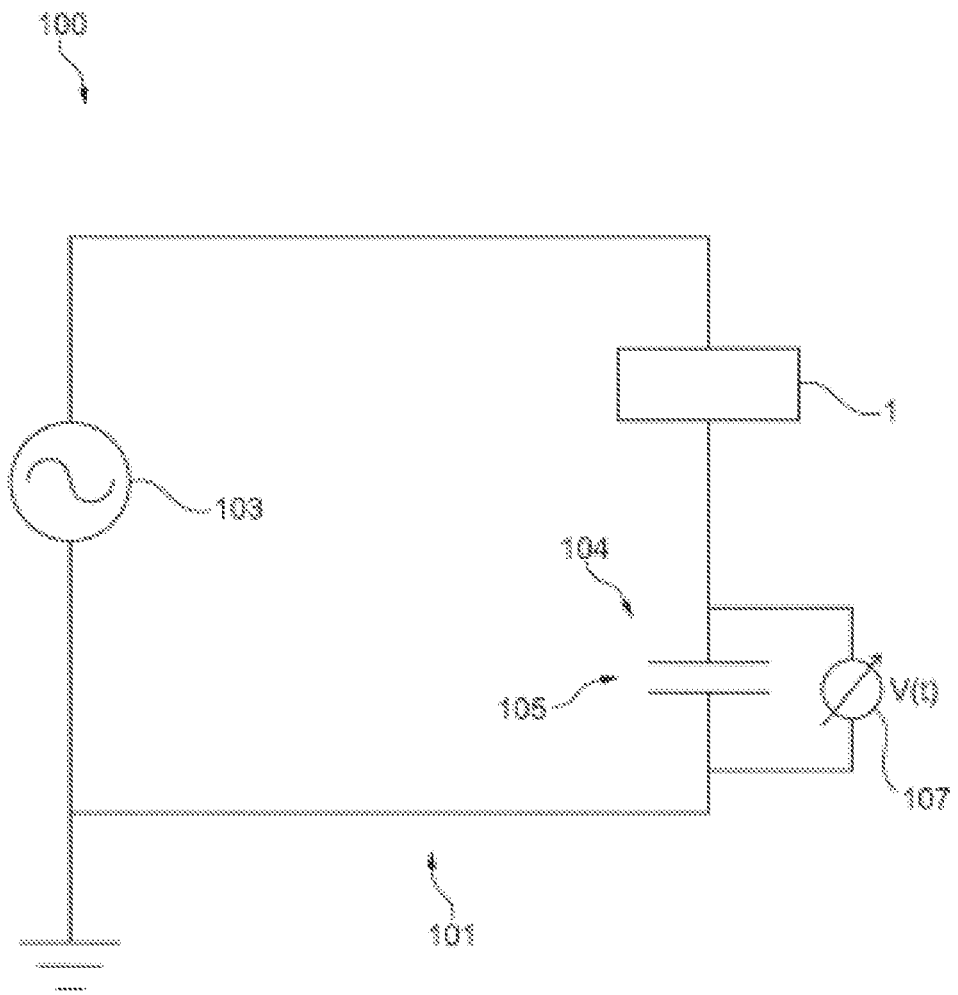
FIG. 2 is a schematic illustration of an embodiment of a plasma source.

FIG. 2 shows a schematic illustration of an exemplary embodiment of a plasma source 100, having an electrode arrangement 1, shown only schematically, for generating a non-thermal plasma. The plasma source 100 also has a control device 101 which is configured to control the electrode arrangement 1. The control device 101 has in particular a voltage source 103, by means of which an alternating voltage can be applied to the electrode arrangement 1 as a control voltage.

In addition, the control device has an electronic proxy structure 104 which can be connected in series with the electrode arrangement 1 and is connected in series in this case. The control device 101 is configured to capture the at least one power parameter on the electronic proxy structure 104 connected in series with the electrode arrangement 1. The electronic proxy structure 104 is designed in this case in particular as a capacitor 105.

At least one value, in particular a mean value, of an alternating voltage V(t)—the proxy voltage—falling across the electronic proxy structure 104 at a certain phase angle of the control voltage is measured as a power parameter, in particular averaged over a plurality of periods of the control voltage, in particular according to the equation (4) given above. The proxy voltage is preferably captured as a function of time by a voltage measuring device 107.

The power parameter is preferably compared with a first, upper target parameter value and a second, lower target parameter value, wherein the at least one action is selected according to whether the at least one power parameter falls within a target parameter range delimited by the first target parameter value and the second target parameter value.

Figure 3:
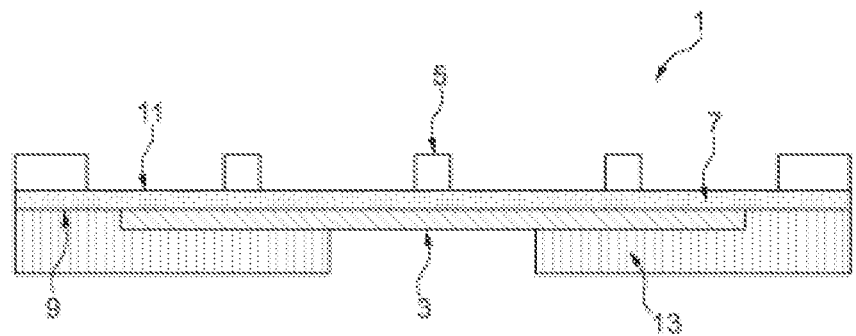
FIG. 3 is a schematic cross-sectional illustration of an embodiment of an electrode arrangement of such a plasma source.

FIG. 3 shows a schematic cross-section and detail illustration of an exemplary embodiment of an electrode arrangement 1 which is configured for generating a non-thermal plasma. The electrode arrangement 1 has a first electrode 3 and a second electrode 5, as well as a dielectric 7, by means of which the first electrode 3 and the second electrode 5 are spaced apart from each other. In particular, the dielectric 7—viewed along a stacking direction—is arranged between the first electrode 3 and the second electrode 5. The stacking direction extends in the vertical direction in FIG. 3.

The first electrode 3 in this case is arranged close against a first side 9 of the dielectric 7, and the second electrode 5 is arranged close against a second side 11 of the dielectric 7, opposite the first side 9.

The second electrode 5 comprises a material that is selected from a group consisting of stainless steel, titanium, tungsten, an electrically conductive plastic, and a conductive adhesive. In addition, the second electrode 5 is compelled against the second side of the dielectric 7, in particular pressed against the second side 11, pushed onto the second side 11, or generally held on the second side 11 of the dielectric 7 under preload.

The electrode arrangement 1 can be produced in a simple, inexpensive manner, and is highly efficient and also highly resistant in particular to oxidation by ozone and to sputtering.

The first electrode 3 preferably comprises copper and/or tin. It is also possible that the first electrode 3 consists of copper or a copper alloy, and/or of tin or a tin alloy. The first electrode 3 particularly preferably has a first layer made of copper or a copper alloy and a second layer made of tin or a tin alloy arranged on the first layer. In this case, the second layer made of tin or a tin alloy is arranged in particular on a side of the first electrode 3 facing away from the dielectric 7—that is, in this case, in FIG. 3, on an underside of the first electrode 3.

A thickness of the first electrode 3 measured in the stacking direction is preferably from at least 1 µm to at most 100 µm, particularly preferably 4 µm, wherein the copper layer of the first electrode 3 preferably has a thickness of 3 µm, and the tin layer of the first electrode 3 has a thickness of 1 µm.

The dielectric 7 preferably has a material or consists of a material selected from a group consisting of Kapton, quartz, glass, ceramic, and aluminum oxide. It preferably has a thickness, measured in the stacking direction, of at least 0.05 mm to at most 0.8 mm, preferably of at least 0.1 mm to at most 0.75 mm, preferably of 0.25 mm.

The second electrode 5 preferably has a thickness, measured in the stacking direction, of at least 5 µm to at most 1 mm, preferably 0.5 mm.

The second electrode 5 and the dielectric 7 preferably have a surface area of 4×4 $cm^2$. The first electrode 3, which is preferably arranged centrally, that is to say in particular in the middle, on the dielectric 7 preferably has a surface area of 3×3 $cm^2$. Other sizes are also possible for the electrode arrangement, since it is particularly modular and very particularly preferably scalable.

The electrode arrangement 1 shown here is particularly flat, and preferably even. However, it is also possible for the electrode arrangement to be curved. The electrode arrangement 1 can be rigid and/or flexible.

The first electrode 3 is preferably coated with an electrical insulating layer 13 at least in some regions. The insulating layer 13 preferably comprises an insulating varnish or consists of an insulating varnish. It is particularly preferably sprayed onto the first electrode 3. In particular, the insulating layer 13 can be formed from a two-component insulating varnish. It preferably has a thickness of more than 3 µm. Alternatively or additionally, it is also possible for the first electrode 13 to be encapsulated with a potting compound.

The first electrode 3 is preferably coated onto the dielectric 7, in particular vapor-deposited. In this respect, it preferably differs from the second electrode 5, which is held on the dielectric 7 under preload and, in particular, is pressed against the second side 11.

In the exemplary embodiment shown here, the dielectric 7 and the second electrode 5 project beyond the first electrode 3 preferably on all sides—viewed perpendicular to the stacking direction. Alternatively, it is also possible that the first electrode 3 and the dielectric 7 protrude beyond the second electrode 5 on all sides, perpendicular to the stacking direction. Furthermore, it is alternatively also possible that the dielectric 7 projects beyond both the first electrode 3 and the second electrode 5 on all sides, perpendicular to the stacking direction.

Figure 4:
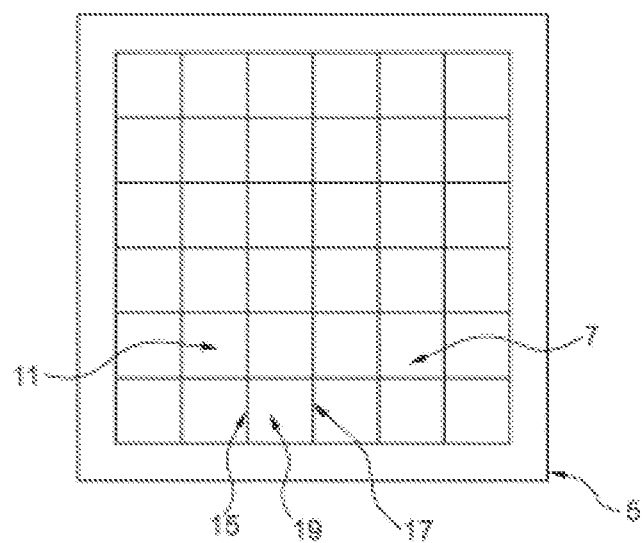
FIG. 4 is a schematic plan view of such an electrode arrangement.

FIG. 4 shows a plan view of the electrode arrangement 1, in particular of the exemplary embodiment of the electrode arrangement 1 according to FIG. 3. Identical and functionally identical elements are provided with the same reference symbols, so that in this respect reference is made to the preceding description. The view of the viewer is directed to the second electrode 5 and the second side 11 of the dielectric 7. The first electrode 3 and the insulating layer 13 are hidden from view of the observer, since they are arranged below the second electrode 5 and the dielectric 7.

The second electrode 5 preferably has a periodic structure made up of a plurality of identical structural elements 15, of which only one is provided here with a reference number, in order to increase the clarity. The structural elements 15 are embodied in this case as squares. Such structural elements 15 can, however, also be designed generally as polygons, triangles, squares, pentagons, hexagons, or higher-ranking polygons, as circles or ellipses, or as one-dimensional shapes, for example as lines, in particular as straight lines, wavy lines, otherwise curved lines or the like. Shapes in the transition area between a one-dimensional and a two-dimensional configuration, for example meandering structures, can also be selected for the structural elements 15. A periodic configuration of the second electrode 5 enables the electrode arrangement 1 to be scaled in a special way, with its generation rate for the non-thermal plasma being able to be scaled more or less linearly with the number of structural elements 15.

Regardless of whether the second electrode 5 has a periodic structure composed of a plurality of identical structural elements 15, or whether only one structural element 15 or a plurality of structural elements 15 configured differently from each other—in particular with regard to size and/or shape—are provided, the second electrode 5 preferably has at least one structural element 15 with at least one recess 19 delimited by edges 17, wherein only one edge 17 and one recess 19 are assigned a reference symbol here for the sake of better clarity. The edges 17 delimiting the recesses 19—measured within a recess 19—preferably have an edge length from at least 0.5 mm to at most 10 mm, preferably from at least 1 mm to at most 8 mm, preferably from at least 2 mm to at most 7 mm, preferably of 5 mm. In particular, the recesses 19, which are square here, preferably have a planar recess area of 5×5 mm$^2$. The embodiment described here advantageously reduces the influence of self-interference of the electric field in corners of the recesses 19, which would otherwise reduce the efficiency of the electrode arrangement 1 in a manner which is relevant.

A web width of the edges 17—measured perpendicular to the stacking direction and perpendicular to the longitudinal extension of an edge—is preferably 0.5 mm. In another preferred embodiment of the electrode arrangement 1, it is preferably provided that the second electrode 5 has a plurality of structural elements 15, and the individual structural elements 15 are spaced apart from each other by at least 0.5 mm to at most 10 mm, preferably from at least 1 mm to at most 8 mm, preferably 5 mm. This also helps to reduce the effect of self-interference.

The electrode arrangement 1 is preferably operated by applying an alternating voltage with an amplitude of at least 2 kV$_{pp}$ to at most 5 kV$_{pp}$ and a frequency of at least 2 kHz to at most 60 kHz, preferably 4 kHz, to the first electrode 3. The second electrode 5 is preferably connected to ground.

In the following, values for the power density of the electrode arrangement 1 in the different operating states are given by way of example, with respect to a volume of approximately 12.5 cm$^3$ enclosed by the spacer. For other enclosed volumes, these values must be selected differently in order to obtain the same operating states: The electrode arrangement 1 is preferably operated in a first operating state with a power of less than 0.01 W/cm. In this first operating state, oxygen species dominate the composition of the non-thermal plasma, which is generated by the electrode arrangement 1 in ambient air. In a third operating state, the electrode arrangement 1 is preferably operated with a power of more than 0.05 W/cm. In this third operating state, nitrogen species dominate the composition of the non-thermal plasma. In a second, intermediate state, the electrode arrangement 1 is preferably operated with a power of at least 0.01 W/cm to at most 0.05 W/cm. In this intermediate state, both active oxygen species and active nitrogen species are found in relevant concentration in the non-thermal plasma, wherein the ratio between nitrogen species and oxygen species can be modified by varying the power consumption of the electrode arrangement 1.

The electrode arrangement 1 is preferably operated for a first predetermined time in the first operating state and, after the predetermined time has elapsed, for a second, predetermined time in the second operating state or in the third operating state.

The electrode arrangement 1 is preferably used to inactivate pathogenic germs, in particular bacteria, fungal infections, in particular skin mycosis and/or athlete's foot, prions, biofilms and/or viruses. These can be inactivated in particular on surfaces, be they inanimate surfaces or surfaces of living beings, in particular plants, animals and/or humans. This is particularly relevant for skin surfaces for the purpose of disinfection or sterilization, and/or for wound treatment.

A large series of measurements was carried out in an environmental chamber in order to determine the correlation between the "real plasma power" and the "proxy measurement," using the circuit diagram shown in FIG. 2

The result of hundreds of such measurements shows that there is a very good correlation between the real and the proxy determination of the plasma power, and that the variation between different plasma sources 100 and/or electrode arrangements 1 of the same design is very low.

The good correlation exists for all environmental conditions that were in the test range.

A preclinical study was carried out with the plasma source 5 in order to determine a safe therapeutic window for treatments.

First, efficacy studies were carried out. It was found that the plasma source 5 very effectively inactivates bacteria—including multi-resistant germs—and fungi. High reductions of four to five orders of magnitude are achieved in such cases, within a treatment duration of only 60 seconds.

Further research showed that bacterial biofilms can also be inactivated. Reductions of three orders of magnitude were achieved within 60 seconds of treatment. A complete reduction could be achieved after a treatment time of 10 minutes.

Furthermore, safety examinations were carried out, in particular vitality examinations on eukaryotic cells (primary fibroblasts and keratinocytes), as were mutagenicity tests, wound healing assays (to analyze the proliferation of cells), and examinations on ex vivo skin (histology, apoptosis or necrosis analysis).

These studies show that even in the worst case scenario of individual eukaryotic cells, there is no damage with treatment periods of up to 3 minutes. The mutagenicity tests did not show any induction of mutations for any plasma treatment duration (tested up to 5 minutes), and the ex vivo skin tests also showed no damage for any plasma treatment duration. This suggests an even larger therapeutic window than specified here.

With the method described here, in particular an initial verification of an electrode arrangement for generating a non-thermal plasma is possible, which in particular significantly increases the reliability of the operation of the electrode arrangement itself and of each of the uses of the electrode arrangement.

The invention claimed is:

1. A method for testing an electrode arrangement (1) for generating a non-thermal plasma, comprising the following steps:
   determining at least one power parameter which characterizes a plasma power of the electrode arrangement (1);
   comparing the at least one power parameter with at least one predetermined target parameter value, and obtaining a comparison result, wherein the at least one predetermined target parameter value of the electrode arrangement (1) is stored with a dependence on at least one operational parameter in a characteristic map, from which the at least one predetermined target parameter value can be read according to the at least one operational parameter, wherein the at least one operational parameter is selected from a group consisting of an ambient temperature of the electrode arrangement (1) and a relative humidity in an environment of the electrode arrangement (1); and
   assessing the functionality of the electrode arrangement (1) on the basis of the comparison result.

2. The method according to claim 1, characterized in that at least one action is selected according to the comparison result, wherein the action is selected from a group consisting of outputting an "OK" signal, outputting an "action required" signal, outputting a "not OK" signal, notifying an operator of the electrode arrangement (1) of a current plasma power, adapting an operating time of the electrode arrangement (1) to the comparison result, terminating an operation of the electrode arrangement (1), and continuing the operation of the electrode arrangement (1) without further action.

3. The method according to claim 1, characterized in that the method is carried out immediately after the electrode arrangement has been put into operation.

4. The method according to claim 3, characterized in that the method is carried out before the electrode arrangement is used.

5. The method according to claim 1, characterized in that the at least one power parameter is captured on an electronic proxy structure (104) connected in series with the electrode arrangement (1).

6. The method according to claim 5, characterized in that at least one value of a proxy voltage falling across the electronic proxy structure (104) at a specific phase angle of a control voltage applied to the electrode arrangement (1), in particular at a zero crossing of the control voltage, is measured as the at least one power parameter.

7. The method according to claim 6, characterized in that an average value of the proxy voltage at the specific phase angle of the control voltage, averaged over multiple, in particular a plurality of, periods of the control voltage is determined as the at least one power parameter.

8. The method according to a claim 5, characterized in that a capacitor (105) is used as the electronic proxy structure (104).

9. The method according to claim 1, characterized in that the at least one power parameter is compared with a first, upper target parameter value and with a second, lower target parameter value, wherein the at least one action is selected according to whether the at least a power parameter falls within a target parameter range delimited by the first target parameter value and the second target parameter value.

10. The method according to claim 1, characterized in that the electrode arrangement (1) is operated for a predetermined period of time before the at least one power parameter is determined.

11. The method according to claim 1, characterized in that the comparison result and/or the at least one power parameter is/are logged for later retrieval in an electronic memory device of the electrode arrangement (1).

12. The method according to claim 11, characterized in that the comparison result and/or the at least one power parameter is/are logged for later retrieval in the electronic memory device of the electrode arrangement (1) with at least one metadata item.

13. The method according to claim 1, characterized in that the electrode arrangement (1) is configured to generate surface micro-discharges in ambient air.

14. The method according to claim 13, characterized in that the electrode arrangement (1) comprises a first electrode (3), a second electrode (5), and a dielectric (7), wherein the first electrode (3) and the second electrode (5) are spaced apart from each other by the dielectric (7) and are each arranged in direct mechanical contact with the dielectric (7).

15. The method according to claim 14, characterized in that the first electrode (3) is a planar electrode (3).

16. The method according to claim 14, characterized in that the second electrode (5) is a planar electrode (5).

17. The method according to claim 13, characterized in that a high voltage, in particular an alternating voltage, is applied to the first electrode (3), and the second electrode (5) is connected to ground.

* * * * *